(12) United States Patent
De Frutos Escrig et al.

(10) Patent No.: US 6,429,323 B1
(45) Date of Patent: Aug. 6, 2002

(54) METHOD FOR CONTINUOUS PRODUCTION OF PROPYLENE OXIDE AND OTHER ALKENE OXIDES

(75) Inventors: Ma Pilar De Frutos Escrig, Madrid; Ana Padilla Polo, Getafe; Jose Migel Campos Martin, Madrid, all of (ES)

(73) Assignee: Repsol Quimica, S.A. (ES)

( * ) Notice: Subject to any disclaimer, the term of this patent is extended or adjusted under 35 U.S.C. 154(b) by 0 days.

(21) Appl. No.: 09/598,933

(22) Filed: Jun. 21, 2000

(30) Foreign Application Priority Data

Aug. 6, 1999 (EP) .............................. 99500140

(51) Int. Cl.$^7$ ........................................... C07D 301/06
(52) U.S. Cl. ....................................... 549/533
(58) Field of Search ........................... 549/533

(56) References Cited

U.S. PATENT DOCUMENTS 5,214,168 A * 5/1993 Zajacek et al.

\* cited by examiner

Primary Examiner—T. A. Solola
(74) Attorney, Agent, or Firm—John C. McMahon

(57) ABSTRACT

Alkene oxides are produced in a continuous integrated two-,step process performed in liquid phase. Step I comprises the oxidation of a secondary alcohol with molecular oxygen to generate hydrogen peroxide at moderate temperature and pressure. This reaction mixture is introduced directly to an olefinic substrate maintained in organic solvent at elevated pressure. During step II of the procedure the olefins undergo epoxidation by the hydrogen peroxide in the presence of a catalyst of titanium-impregnated, amorphous silica. The integrated process requires no intermediate purification or enrichment step and it is particularly well adapted to the production of propylene oxide.

23 Claims, 1 Drawing Sheet

METHOD FOR CONTINUOUS PRODUCTION OF PROPYLENE OXIDE AND OTHER ALKENE OXIDES

BACKGROUND OF THE INVENTION

1. Field of the Invention

This invention relates to the field of manufacturing oxides of alkenes and the generation of peroxides for use in such manufacture. More particularly, it relates to an integrated, continuous, liquid phase process in which a first reaction generates hydrogen peroxide in organic solution; this reaction mixture is used for epoxidation of an olefin, which is also maintained in organic solution. When hydrogen peroxide is generated under the conditions disclosed and the reactions are coupled according to the invention, the reaction mixture may be used directly as a reagent for the second reaction. Thus there is no requirement for extraction or separation of hydrogen peroxide after the first step nor for removal of products of this first reaction such as ketones. The second reaction is maintained in liquid phase by the use of an organic solvent in combination with appropriate temperature and pressure conditions. This epoxidation reaction also requires the presence of a titanium-impregnated, amorphous silica catalyst, which is described below as a part of the invention.

2. Background of the Invention

Olefinic epoxides, such as ethylene oxide and propylene oxide, are soluble in organic solvents but insoluble in aqueous solutions. The production of epoxides from olefins results in commercially valuable products that have multiple uses in the plastics and chemical industries. The broad range of olefinis available as starting material is capable of generating epoxides which serve as intermediates in the preparation of a vast spectrum of chemical compounds.

The industrial epoxidation of olefins is performed by the reaction of the olefin with a peroxide reagent. Either hydrogen peroxide or an organic peroxide may be used, although the appropriate reaction conditions, the attainable reaction efficiency and the stability of these reagents varies substantially. If the peroxide reagent is generated from organic precursors as part of an integrated process of olefin epoxidation, economies may be realised by reducing the handling and storage of these chemicals.

The integrated process must couple two reactions: a first reaction that would generate peroxide efficiently within a liquid organic medium and a second reaction that would introduce the peroxide product to an olefin maintained in liquid phase by solvent under pressure. Successful integration of the two reactions requires that the conditions of each should be selected so that the products of the first reaction are compatible with the physical and chemical conditions of the second. Besides balancing effects of temperature and polarity upon solubility and stability, the reaction conditions must minimise undesirable secondary reactions of the peroxide with the various organic substrates, products and solvents employed in an integrated process. This is a particular problem if hydrogen peroxide is used as an reagent or intermediate product, generally requiring that the hydrogen peroxide is isolated from reagents and co-products before it can be used in the epoxidation reaction. Previously, the practicality of combining and integrating these reactions has been compromised by the relatively low yields of hydrogen peroxide obtained from the organic reactions known in the art and by the violent oxidising properties of hydrogen peroxide: although commercially available in aqueous solutions of up to 70% by weight, hydrogen peroxide is unstable and is capable of reacting explosively with organic materials.

Hydrogen peroxide may nevertheless be used as an oxidising agent for the production of epoxides from olefins, but it is especially desirable to generate this reagent at the time and the location in which it is required, in order to minimise hazardous handling and storage operations. Moreover, if the kinetic advantages of the strongly oxidising properties of hydrogen peroxide are to be exploited by using this reagent in the epoxidation reaction, its capacity to undergo side reactions with other components of the reaction mixture must be limited. Thus substantial benefits may be gained by integrating into a combined reaction process the production of hydrogen peroxide and its utilisation for olefin epoxidation. Yet the detrimental complications that such a procedure would generate—such as the additional potential for side-reactions in which the hydrogen peroxide may participate—must also be addressed.

Further advantages are to be derived by generating the hydrogen peroxide from organic reagents in organic solution: the reagent may then be mixed rapidly and efficiently with the olefin and the solvent, permitting the epoxidation reaction rate to be controlled accurately. The ability to exercise fine control over the rate of this exothermic reaction is a prerequisite for the development of continuous methods of olefin epoxidation, which offer the potential for additional economic benefits through increased efficiency, particularly when associated with an integrated production process.

The nature of the epoxidation catalyst is also critical for the success of the integrated process. A solid catalyst provides advantages of simple recovery, for example by filtration, prior to regeneration. The supporting structure for transition metal catalysts of epoxidation reactions fall into two categories, possessing either a porous, crystalline zeolite or silicalite structure which possess the additional properties of a 'molecular sieve', or the structure of a solid, amorphous silica or alumina. Catalysts in the former group are expensive and limit the useful range of olefins with which they may be used because the diameter of the pores in the support limit access to the catalyst's active centres. Catalysts of the latter group have been used with less reactive organic peroxides as oxidising agents, but if hydrogen peroxide is the oxidant they lower selectivity by expanding the spectrum of significant side reactions that occur, especially if reactions are combined in series. Substantially reduced efficiency and contaminated products are the result.

3. Description of the Prior Art

Industrial epoxidation processes are generally performed by introducing hydrogen peroxide or an organic peroxide to the olefin while the latter is dissolved in an organic solvent. Development of integrated processes in which the peroxide reagent is produced in situ has been discouraged by the technical difficulties outlined above.

Nevertheless, there have been disclosures of industrial olefin epoxidation procedures in which the peroxide reagent is generated immediately prior to the epoxidation reaction as part of an integrated process. These processes lack either an adequate solution to one or more of the technical problems addressed by the present invention, or suffer from another disadvantage, as indicated in more detail below.

In U.S. Pat. No. 5,214,168 Zajacek and Crocco disclose an integrated process of air oxidation of an aryl-substituted secondary alcohol, followed by the use of the oxidation product for epoxidation of an olefin in the presence of a crystalline titanium silicalite catalyst.

European Patent No. EP 0 526 945 discloses an integrated method of olefin epoxidation utilising hydrogen peroxide that is generated in situ. The hydrogen peroxide is produced from a redox reaction between oxygen or air and an alkylanthrahydroquinone. It then reacts with the olefin in the presence of a titanium silicalite catalyst and a specific mixture of organic solvents, comprising one or more aromatic hydrocarbons, one or more polar organic compounds of high boiling point and an alcohol of low molecular weight (methanol). The precise reasons for using this complex mixture of solvents are not disclosed in the publication. Yet the rationale may be related to the low solubility exhibited by alkylanthroquinones and alkylanthrahydroquinones when dissolved together: this characteristic limits the maximum quantity of hydrogen peroxide that can be generated by any specified volume of reactor.

Clerici & Ingallina, European Patent No. 0 549 013, disclose, inter alia, a process of olefin epoxidation by hydrogen peroxide in the presence of titanium silicalite that uses an aqueous mixture of alcohols as solvents for extracting the hydrogen peroxide generated in an alkylanthrahydroquinone redox system. However, the low solubility of the alkylanthrahydroquinones in the solvents used for the reaction significantly limits the commercial utility of this process.

Rodriguez & Zajacek, U.S. Pat. No. 5,463,090, disclose an integrated process for the production of epoxides based upon molecular oxygen oxidation of an alkylammonium salt of a sulphonic acid substituted anthrahydroquinone. The reaction product from the oxidation contains hydrogen peroxide and is used for olefin epoxidation in the presence of a titanium silicalite catalyst. Although the oxidation and epoxidation may be performed concurrently, the sulphonic acid-substituted anthraquinone alkylammonium salts are highly soluble in polar protic media such as water and lower alcohols. Consequently, the difference in solubility between these reagents and the olefin reactants, in the various solvents of interest, would be expected to substantially diminish the rate and extent of the reaction. Differential distillation is used to recover the aliphatic epoxide product.

U.S. Pat. No. 5,384,418, European Patent Applications No. EP 0 568 336 and European Patent Application No. EP 0 732 327 disclose procedures for the epoxidation of olefins in which the oxidation of secondary alcohols by oxygen or air generates hydrogen peroxide and the corresponding ketone. The resulting solution of hydrogen peroxide is used, following intermediate treatment, for olefin epoxidation in the presence of crystalline titanium silicalite catalyst, with methanol acting as solvent.

A discussion of the art relating to epoxidation catalysts is provided below, following the descriptions of the two reactions that are incorporated into the integrated process for producing olefin oxides.

Reviewing the art associated with the first reaction of the combined process, it is known that hydrogen peroxide may be generated from the oxidation of secondary alcohols by molecular oxygen:

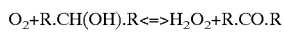

When optimising the preparation of hydrogen peroxide from secondary alcohols the preferred product, besides the hydrogen peroxide itself, is the corresponding ketone. Thus the most commonly employed alcohol is isopropanol, with acetone being the major organic product: catalysts may be used but are not required for the industrial process. Yet in practice side reactions cause major difficulties when attempting to obtain high yields of hydrogen peroxide, and organic peroxides are generated as typical by-products.

Oxidation of isopropanol yields mixtures of organic peroxides and hydrogen peroxide: U.S. Pat. No. 2,869,989; U.S. Pat. No. 3,156,531; U.S. Pat. No. 3,294,266 and British Patent 758,907. Other secondary alcohols used as starting materials for hydrogen peroxide production include 1-phenylethanol and cyclohexanol: U.S. Pat. Nos. 2,871,102 to 2,871,104. Production of hydrogen peroxide by liquid phase oxidation of 1-phenylethanol with molecular oxygen, in which the hydrogen peroxide is recovered in organic solution, is disclosed in U.S. Pat. Nos. 5,254,326, 4,975,266 and 4,897,252. The oxidation of secondary alcohols with high boiling points such as diaryl methanols, in which the hydrogen peroxide is isolated in vapour form is described in U.S. Pat. No. 4,303,632.

Under industrially suitable conditions of temperature and pressure the production of hydrogen peroxide by oxidation of secondary alcohols with liquid-phase molecular oxygen is enhanced by admixing primary alcohols and/or ethers with the secondary alcohol. Not only is the reaction rate increased but also selectivity of the reaction towards hydrogen peroxide is improved. Thermal decomposition of hydrogen peroxide is decreased and side-reactions with other reactants are diminished. (Hydrogen peroxide is capable of reacting with both the secondary alcohols used as starting material and with the ketones produced during the oxidation reaction.) This approach to solving the problem of simultaneously achieving high reaction rates while retaining selectivity to hydrogen peroxide is disclosed in European Patent Application No. EP 0 839 760.

Reviewing the art relating to the second reaction of the combined process, it is known that the epoxidation of unsaturated olefinic compounds may be achieved with a broad range of reagents. Organic hydroperoxides may be used to obtain olefin epoxides in liquid phase: as an industrial process this generates the alcohol derivatives of the initial organic hydroperoxide as coproducts. Epoxidation of unsaturated olefinic compounds using hydrogen peroxide is another well-recognised reaction, which requires the use of a catalyst to be performed economically as an industrial process:

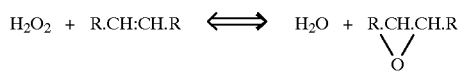

Currently many of the catalysts developed for this reaction comprise synthetic zeolites: crystalline silicalite and/or alumina structures incorporating transition metals and their oxides. Crystalline silica is impregnated with titanium salts, such that titanium is incorporated into the crystal lattice. These titanium silicalite catalysts may require activation by being calcined in an oxidising atmosphere at elevated temperature to generate titanium oxide at the active centres. Catalysts designed to improve the efficacy of olefin epoxidation reactions are disclosed, for example, by U.S. Pat. Nos. 4,41,501, 4,666,692, 4,701,428, 4,824,976 and 4,833, 260.

Although the selectivity for the epoxide is relatively high when using these crystalline titanium silicalite catalysts, non-selective opening of the epoxide's oxirane ring also occurs during the reaction. Selectivity for epoxide may be augmented by treating the catalyst with an alkaline agent to neutralise the acid centres of the catalyst surface that are responsible for the undesirable ring-opening process: Clerici & Romano, EP 0 230 949. Non-basic salts such as lithium chloride, sodium nitrate and potassium sulphate suppress the oxirane ring opening mechanism and improve selectivity for the olefin epoxide: Crocco & Zajacek, EP 0 712 852.

Methanol is generally favoured as a solvent for the olefin epoxidation reaction because of its capacity to act as a proton donor, so that it is also considered to be a co-catalyst: M. G. Clerici et al., 1991, *J. Catal.* 129; 159. However, the use of this solvent is problematical in the epoxidation of propylene, specifically in the later stages of purifying the product, because of the proximity of its boiling point with that of propylene oxide. Alternative reagents and solvents permitting differential distillation may be employed, as disclosed in Deguchi, et al., EP 0 673 935.

Synthetic titanium derivatives of zeolite analogues, such as the crystalline silicalites, are known in the art and are frequently used for organic oxidation reactions using hydrogen peroxide. However, the restrictive pore diameter of the crystalline titanium silicalites (5.6×5.3 Å) denies access to the active centres of such catalysts by many larger olefin molecules and consequently epoxidation of these olefins, for example norbornene, will not be proceed efficiently using such catalysts.

Moreover, when used for epoxidation of olefins using hydrogen peroxide the catalytic activity of crystalline titanium silicalites is significantly more selective towards olefin epoxidation than is that of catalysts in which titanium is supported on amorphous, solid silica structures (as employed in the epoxidation reaction of the present invention). Of particular relevance to integrated processes of olefin epoxidation, the disclosure of Esposito et al. in U.S. Pat. No. 4,480,135 teaches that both primary and secondary alcohols are readily oxidised by hydrogen peroxide in the presence of a crystalline titanium silicalite catalyst. That such undesirable reactions are not observed under the restrictive epoxidation conditions of U.S. Pat. No. 5,124,168 indicates that the crystalline titanium silicalite catalysts may vary significantly in selectivity.

All the integrated olefin epoxidation processes described in the art and reviewed above employ for the epoxidation reaction crystalline titanium silicalite catalysts. In addition to the disadvantages associated with these zeolite analogues' activity as molecular sieves, and their apparently variable selectivity, the complexity of synthesising such catalysts results in their commanding an elevated price. That the titanium catalysts also undergo rapid deactivation in the epoxidation reaction medium indicates the advantages to be gained from the development of an epoxidation catalyst that can be regenerated in a simple, industrial-scale process, either by basing it upon an inert agglomerate support, (e.g. EP 0 200 260) or by modifying its method of preparation (e.g. EP 0 638 362). An alternative would be to develop a catalyst that remains active for an extended period.

Epoxidation catalysts in which titanium is supported on solid amorphous silica are known to be effective in the epoxidation of olefins by organic hydroperoxides, as disclosed in, for example, U.S. Pat. No. 3,642,833, 3,923,843, 4,021,454 and 4,637,342. However, for industrial applications these catalysts have proven ineffective for the epoxidation of olefins using hydrogen peroxide as oxidising agent because they lack the requisite specificity and selectivity towards the desired olefin epoxide. Nevertheless, WO 94/23834 discloses synthesis of a product of silica and titanium fluoride under specific experimental conditions which catalyses a broad variety of chemical oxidation reactions, including the epoxidation of olefins by oxidation with either organic peroxides or hydrogen peroxide. As would be expected, this catalyst provides only a moderate selectivity towards epoxide. Surprisingly, however, undesirable side-reactions are not observed when the olefin epoxidation reaction is catalysed by the titanium-impregnated amorphous silica catalyst of the present invention. The selectivity towards epoxide that is displayed by the catalyst of the present invention is particularly unexpected given the broad spectrum of primary and secondary alcohols, ketones and solvents that may be present in the epoxidation step of the integrated process. This highly selective catalytic activity is obtainable by using the present invention's particular method of preparing this robust catalyst of titanium supported on solid amorphous silica, which suggests that the method selected to prepare such catalysts may influence both the catalyst's structure and the selectivity of its catalytic activity.

Alternative catalyst structures may incorporate alumina, which may be substituted with ammonium, alkali metal or alkaline earth metal ions, in order to increase accessibility to the active centres or to reduce the oxirane ring-opening side reactions, although selectivity for epoxide may be compromised: U.S. Pat. No. 5,412,122, 5,374,747, and 5,621,122, EP 0 659 685.

Although individual methods are known in which one or other of the two component reactions can be performed in liquid phase, a combination of such liquid phase methods is perceived to be highly desirable: i.e. a first liquid phase stage in which hydrogen peroxide is generated through the oxidation of a secondary alcohol by molecular oxygen followed by a second liquid phase stage in which the hydrogen peroxide reacts with the olefin, which must normally be dissolved in an organic solvent to remain liquid. A combined two-step method would provide economic and logistical advantages of reduced handling and storage of intermediate reactants, particularly in view of the chemical instability of hydrogen peroxide and its potentially hazardous nature.

Yet in order for such a combined process to operate effectively and economically on an industrial scale optimum efficiency would be required from the individual component reactions so that yields of the appropriate products from each of the reactions were maximised. If either reaction were performed under sub-optimal conditions, not only would the generation of by-products from the first step contaminate the subsequent reaction and substantially reduce the yield obtained from the second step, but poor efficiency in the second step would jeopardise the industrial applicability of the combined process.

4. Objects of the Invention

The invention addresses the requirement for a convenient, safe, effective and economical method for generating olefin epoxides from alkenes by providing solutions to the difficulties associated with the implementation of a continuous process which integrates the generation and delivery of hydrogen peroxide with its utilisation for olefin epoxidation.

The invention couples into a single compatible process a first step which is a convenient, effective and economical method for generating hydrogen peroxide in organic solution at high concentration and a second step, an epoxidation reaction that exploits a robust catalyst capable of high selectivity for epoxide with the selected reactants and solvents. Physical conditions for both reactions are selected to permit the combined process to be operated entirely in liquid phase.

By combining these reactions into a single, integrated process the invention must overcome the following problems:

a. the differential solubility of reagents; polarity differences between various reagents and the organic solvents required to maintain the product in solution;

b. the selectivity of peroxide production; the difficulty in obtaining a high percentage of hydrogen peroxide in solution from reactions involving oxidation of organic substrates and employing organic solvents;

c. the reactivity of hydrogen peroxide and its tendency to participate in multiple side-reactions with the organic reagents, products and solvents present;

d. the inefficiency and expense of isolating the peroxide reagent from contaminating alcohol reagents and ketone products before using it in the epoxidation reaction;

e. selective catalysis of the epoxidation step; the requirement for a catalyst capable of catalysing the epoxidation of olefinis by hydrogen peroxide in organic solvents while minimising acceleration of alternative oxidation reactions between hydrogen peroxide and the multiple organic components present in the integrated epoxidation reaction mixture.

Thus in order to combine the reactions required for olefin epoxidation into a single process the invention addresses, inter alia:

i. in the first step, the need to obtain elevated yields and rates of reaction when generating hydrogen peroxide from an organic reagent, such as a secondary alcohol;

ii. the selection of solvent systems for the two reactions that are mutually compatible and which maintain all the reagents in miscible solutions; and iii. in the second step, the need for a catalyst that accelerates the epoxidation reaction itself without catalysing undesirable side reactions of the hydrogen peroxide to a significant extent.

Improving the rate and selectivity of the first reaction enables the resulting organic solution to be used to introduce hydrogen peroxide directly into the second reaction, the epoxidation, in a form in which it is miscible with the organic solvent required to maintain the olefin reactant in the liquid state. Moreover, no intermediate purification steps are necessary when the two reactions are performed under the specified, compatible combination of conditions. The ability to use the organic reaction mixture from the first step directly as a source of hydrogen peroxide for the second, epoxidation reaction requires the development of an appropriately selective catalyst that will minimise the reaction of hydrogen peroxide with the other reagents and reaction products present, including those introduced with the addition of the first reaction mixture. Simplicity and cost-effective preparation and regeneration are additional beneficial characteristics for such a catalyst.

The adaptation of the combined reactions to a continuous, integrated process is achieved by the technological developments described herein and their incorporation into a single, sequentially organised and compatible procedure.

SUMMARY OF THE INVENTION

The present invention provides for a combination of reactions enabling alkene oxides to be produced in a two part, liquid-phase process. By performing the entire process in liquid phase, without the requirement for the purification or enrichment of intermediates or for the removal of by-products, the invention facilitates adaptation of this integrated process for olefin epoxidation to methods of continuous industrial production.

The invention provides for a continuous, integrated process for producing an organic epoxide comprising the following steps: (i) oxidation of a secondary alcohol (reagent A) by molecular oxygen or air; (ii) epoxidation of an olefin by admixing the reaction mixture of step (i) with a solution of the olefin in an organic solvent (reagent B) in the presence of a titanium catalyst supported on amorphous silica at temperatures comprising between 50° C. and 140° C., wherein the titanium catalyst is obtainable by impregnation of silica having a surface area comprising between 50 $m^2$/g and 900 $m^2$/g with a solution of titanium alkoxide and/or titanocene in oxygenated organic solvent (reagent C).

In a further embodiment the invention provides for the rate of the first reaction to be enhanced by the presence of a primary alcohol and/or ether, which also greatly improves selectivity toward hydrogen peroxide. Under these circumstances the reaction may be performed efficiently under moderate temperatures and pressures in the presence of an organic solvent. This solvent maintains the hydrogen peroxide in solution as it is generated so that it may be rapidly and effectively mixed with the organic solution in which the epoxidation reaction occurs.

The second reaction is performed under pressure and at moderately elevated temperatures in the presence of organic solvent. The invention provides for the use of a defined catalyst for the epoxidation, composed of titanium-impregnated, solid, amorphous silica, which enables this reaction to proceed with the desired efficiency and selectivity toward the olefin epoxide. The titanium catalyst is obtainable by the impregnation of silica having a surface area comprising between 50 $m^2$/g and 900 $m^2$/g with a solution of titanium alkoxide and/or titanocene in oxygenated organic solvent. Additionally, other elements could be added to the silica such as germanium, vanadium, etc. These elements may be incorporated onto silica in a prior, separate step from the impregnation with titanium, or the silica may be impregnated with all components together using a combined solution, or subsequently in a separate step after the impregnation with titanium. The resulting titanium-impregnated silica is isolated as a robust, solid, amorphous residue and may be activated by calcination or by treatment with solvents, either prior to use, or for purposes of regenerating used catalyst after recovery from the epoxidation reaction mixture.

In particular, the invention provides a safe, effective and efficient means of producing propylene oxide from two organic solutions, one of which contains propylene and the other being an organic solution of reagents that includes hydrogen peroxide. The latter solution is generated from the oxidation of a secondary alcohol such as 1-phenylethanol by molecular oxygen or air. These two reactions are coupled in a continuous, entirely liquid-phase process.

Figure 1:
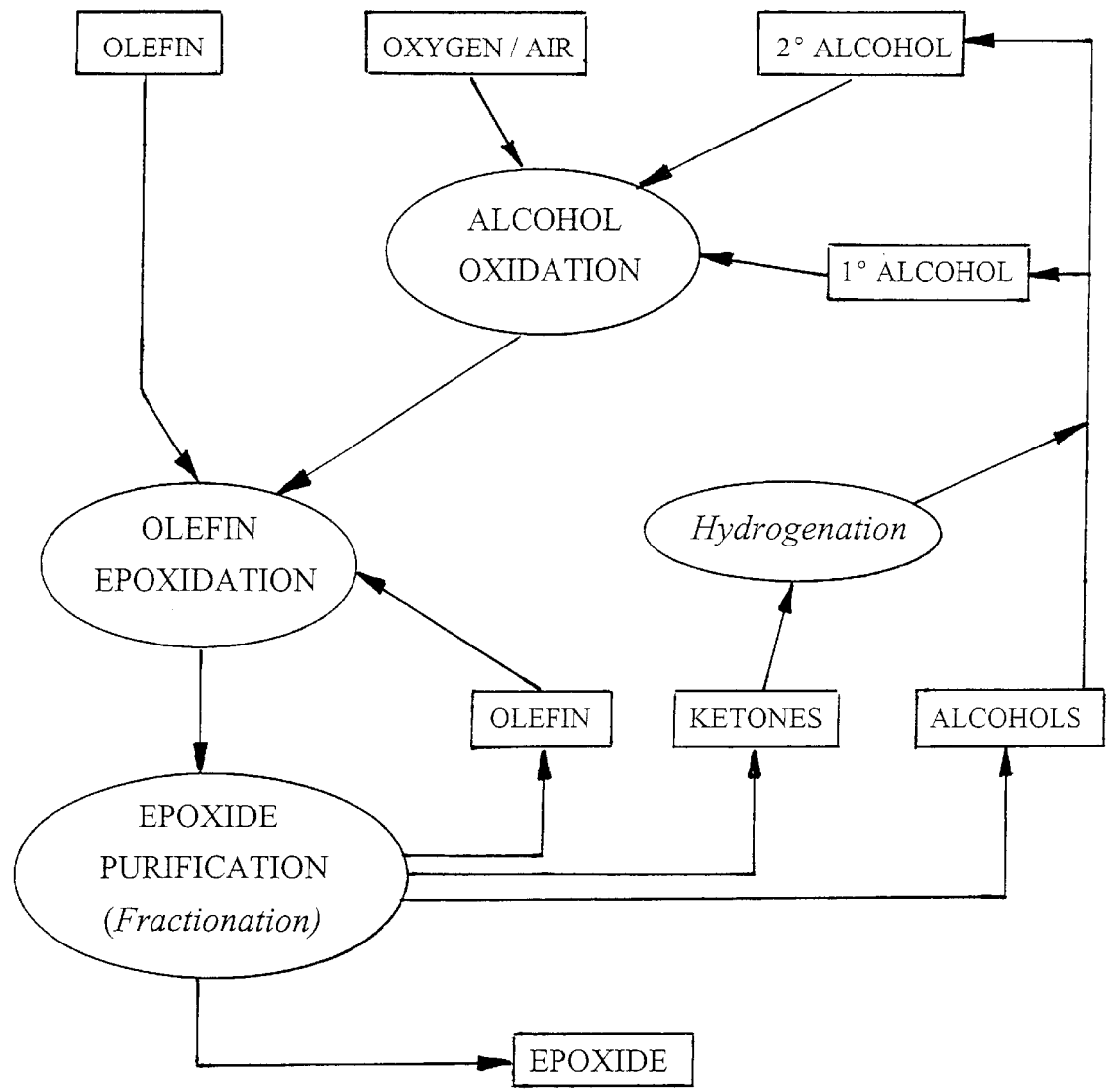
FIG. 1 provides an overview of a preferred embodiment of the continuous, integrated process of the invention. The scheme for epoxidation of olefins using hydrogen peroxide generated in organic solution from a secondary alcohol and molecular oxygen or air is illustrated in the Figure. In the first step the secondary alcohol is oxidised in the presence of a primary alcohol, which improves the selectivity towards hydrogen peroxide production. An ether may be employed in addition to, or in place of the primary alcohol. The reaction mixture resulting from this first step is introduced to an olefin which undergoes epoxidation in the second step of the process. The reaction conditions and catalyst required for this reaction are described elsewhere in this specification.

The reaction mixture from the second step is then fractionated by any of a number of means that are standard within the art, such as differential distillation. As a result of the fractionation, unreacted olefin may be purified and recycled for epoxidation. The fractionation process may also provide for isolation of alcohols and or ketones, present in the epoxidation reaction mixture as reagents, products or solvents. Such fractionation may be employed as a secondary procedure, or as an integral part of the epoxide purification (as illustrated in FIG. 1). Appropriate alcohols that are isolated in the fractionation procedure may be recycled for further use. Ketones may be hydrogenated to their corresponding alcohol by methods well known in the art and these alcohols recycled through the reaction steps as appropriate.

The figure portrays reagents within boxes, and reactions within elipses. The arrows indicate ingredients required and/or generated by the individual steps of the procedure. The major reagents and reactions are shown in bold typeface, as are the arrows depicting the major additions (ingredients required) and products (ingredients generated) associated with the individual steps of the process.

DETAILED DESCRIPTION OF THE INVENTION

The invention provides an effective process for obtaining organic epoxides by a coupled two-reaction procedure, that is capable of being performed entirely in liquid phase. The reaction solution of the first reaction may be used directly as a reagent for the second reaction. There is no requirement for purification or enrichment of intermediates, nor for the removal of by-products from the production of hydrogen peroxide, or its subsequent reaction with the initial reagents or other products. The second reaction uses the products of the first reaction to oxidise an alkene maintained in solution by an organic solvent at moderately elevated temperature and pressure. This epoxidation reaction is performed in the presence of a titanium-impregnated, amorphous silica catalyst prepared by a specified protocol.

According to the present invention, the coupled peroxide-generating reaction and epoxidation reaction may be performed in a manner that is continuous, using an appropriate reactor: a twin-chambered tank reactor for example, permitting controlled addition of the peroxide-containing reaction mixture from a first reaction (in the first chamber) into a second chamber. This second chamber would house the epoxidation reaction, with forced mixing of the contents and agitation therein of a suspension of catalyst particles. Reactant solutions may be added in combination or sequentially. For example, either the reaction mixture generating hydrogen peroxide, or the olefin, or both of these reagents may be added to the reactor incrementally.

The olefin epoxide product may be separated from the epoxidation reaction mixture by standard methods known in the art, such as liquid-liquid extraction, extraction by distillation and fractional distillation. These operations may be performed on the entire reaction mixture, and may follow removal of suspended catalyst. Alternatively, the epoxide product may be separated from part or all of the reaction mixture according to a periodic programme, or from a part of the reaction as a component of a continual operation.

Other components of the epoxidation reaction mixture may be isolated by recognised means of fractionation, such as differential distillation, either as part of the process of purifying the olefin epoxide or as a distinct fractionation procedure, preceding or following removal of the epoxide. Ketone products may be further fractionated, either prior to a hydrogenation procedure or following hydrogenation, in order to form the corresponding alcohol. Unreacted alcohols and alcohols generated from side reactions or from the hydrogenation of ketone products may also be further fractionated. Thus purified alcohols may be obtained for recycling as reagents, additives or solvents in the first or second reactions. The solid catalyst may be separated from the epoxidation reaction mixture for regeneration by methods well known in the art, such as filtration. Regeneration of the catalyst is described in greater detail below.

The integrated process for the industrial production of olefin epoxides that is provided by the invention solves a similar problem to that addressed, in part, by the integrated olefin epoxidation procedures disclosed in the prior art as described above. In addition, the present invention incorporates improvements to the component reactions of the integrated process which increases their rate, selectivity and compatibility, resulting in significant enhancement of the process as a whole. Certain of these improvements, such as the incorporation of a primary alcohol and/or ether additive into the peroxide-generating reaction provide benefits that are realisable in the individual reactions as well as in the integrated process. Other benefits provided by the process of the present invention are particular to the combination of reactions employed in the integrated process, one example being the utilisation in the epoxidation reaction of the titanium-impregnated, amorphous silica catalyst described herein. This catalyst not only enhances the rate and selectivity towards epoxide of the olefin epoxidation reaction performed in isolation, but it also greatly enhances that selectivity in the epoxidation stage as part of the integrated process. The enhanced selectivity provided by the titanium-impregnated amorphous silica catalyst of the present invention is evident from the data disclosed by the included Examples. The observed selectivity towards epoxide is surprising in that when the reaction mixture from the invention's first reaction is added to the epoxidation mixture, it not only contains elevated concentrations of hydrogen peroxide but it also contributes additional organic reactants (i.e. a secondary alcohol reagent, a secondary ketone product and optionally a primary alcohol additive) which are capable of reacting with the hydrogen peroxide in competition with the olefin.

Thus the titanium-impregnated, amorphous silica catalyst of the present invention is required to provide a high degree of selectivity towards the olefin epoxide, and this is achieved under the invention's recommended conditions for the epoxidation. These include a first, peroxide-generating reaction mixture that preferably includes both primary and secondary alcohols as components in order to produce elevated concentrations of hydrogen peroxide in the organic solvent. This strongly oxidising solution is then employed as a reagent in the catalysed epoxidation reaction, even though the oxidising solution contains reagents, products and solvents that are capable of reacting with the hydrogen peroxide.

In particular, the distinctions that differentiate the present invention from U.S. Pat. No. 5,214,168, which also discloses an integrated process for producing olefin epoxides, illustrate significant advantages of the present invention:

i. By improving the selectivity of the peroxide-generating reaction the present invention permits greater concentrations of hydrogen peroxide to be generated in the first reaction mixture which is then used as oxidant solution for the epoxidation reaction. The overall yield and efficiency of the process may therefore be increased, provided that the hydrogen peroxide at these elevated concentrations can be maintained in solution by the selected organic solvent and can be prevented from reacting with other components of the reactions making up the integrated process. The current invention successfully addresses each of these requirements.

ii. By utilising a catalyst of titanium-impregnated, amorphous silica that may be prepared by the distinct procedure described in this specification, the advantages of using a robust, inexpensively prepared, easily regenerated solid catalyst are combined with particularly favourable catalytic properties, that do not exclude epoxidation of olefins possessing larger molecular structures. The catalyst of the present invention is capable of selective enhancement of the olefin epoxidation reaction in the presence of the numerous alternative substrates, with which the hydrogen peroxide might otherwise react, that is provided by the implementation of the integrated process: i.e. by using the reaction mixture from the first reaction as oxidant solution for the second, epoxidation reaction without an intervening purification step.

Step I

The first reaction of the integrated process is the production of hydrogen peroxide in organic solution by the oxidation of a secondary alcohol by molecular oxygen or air, and is preferably performed entirely in liquid phase. The secondary alcohols that may be oxidized to hydrogen peroxide plus ketones in this step are also referred to in this specification as 'reagent A'.

Hydrogen peroxide is available as a standard commercial product in aqueous solution at approximately 30%. But in addition to the costs associated with safety and storage of highly reactive oxidising reagents, it has the disadvantage of being relatively expensive. Consequently, the process of the current invention presents a method of using hydrogen peroxide dissolved in organic solvents, with preferred concentrations of hydrogen peroxide being between 1% and 15%. These dilute solutions of hydrogen peroxide in organic solvents may be obtained at low cost, for example by oxidation by molecular oxygen of secondary alcohols (e.g. isopropanol, 1-phenylethanol and the alkylanthrahydroquinones).

The inventors have disclosed elsewhere a liquid phase process in which primary alcohols and/or esters are added to the reaction mixture in order to increase the selectivity towards hydrogen peroxide: European Patent Application No. EP 0 839 760. This process overcomes the problems of by-product generation and reduced hydrogen peroxide yield without employing elevated temperatures or pressures. By providing the hydrogen peroxide product at relatively high selectivity, and dissolved in an organic solvent, the product mix generated under the conditions recommended for the first reaction has been determined to be appropriate for use as the oxidising reagent for the second reaction. (Not only are the solutions miscible, but as described below, under the recommended epoxidation conditions the catalyst of the second reaction is highly selective for the olefin epoxide product. This selectivity exists in spite of the variety of potential side-reactions in which the hydrogen peroxide could participate given the variety of organic reagents, products and solvents that are available in the reaction mixture of the integrated second step.)

Preferred reaction conditions for performing the first reaction, the oxidation of the secondary alcohol (reagent A), are moderate temperature (between approximately 60° C. to 160° C., and preferably between 80° C. and 140° C.) and partial pressures of oxygen elevated sufficiently for reasonable reaction rates to be achieved ($pO_2$ in the feeding gases of approximately 0.1 kg cm$^{-2}$ to 15 kg cm$^{-2}$, and preferably from 0.2 kg cm$^{-2}$ to 5 kg cm$^{-2}$), while overall pressure in the reaction vessel must be adequate to maintain the reaction mixture in liquid phase (generally between 1 kg cm$^{-2}$ and 40 kg cm$^{-2}$ and preferably between 2 kg cm$^{-2}$ and 15 kg cm$^{-2}$. Under these conditions, a concentration of hydrogen peroxide of between 1% and 15% by weight is generated within the organic solution in which the secondary alcohol (reagent A) is oxidised by molecular oxygen or air. The reaction is exothermic and requires removal of reaction heat by any of the appropriate methods familiar to those of skill in the art, including partial evaporation and condensation of the components of the reaction mixture. Metallic contaminants or other products that promote peroxide decomposition must be rigorously excluded from the reaction mixture. Peroxide stabilizing agents may be incorporated, examples being alkaline metal salts and hydroxides, sodium stannate, sodium pyrophosphate, organic phosphonates, ethylenediaminotetraacetic acid (EDTA), dipicolinic acid, benzoic acid, aminotri(methylenephosphonic) acid, 1-hydroxyethylidene-1,1-diphosphonic acid, ethylenediaminotetra(methylenephosphonic) acid, pyrophosphoric acid and their salts and derivatives.

The secondary alcohols (reagent A) that may be oxidized to hydrogen peroxide plus ketones in this step include organic compounds which contain at least one carbon atom bonded to: one hydrogen atom, one hydroxyl group and two organic radicals; of the general formula:

$$R^1.CH(OH).R^2$$

where $R^1$ and $R^2$ may be the same or different, each being selected from alkyl, arylatkyl (i.e. alkyl groups substituted with aryl groups) and/or aryl groups. Among the preferred alkyl groups are the $C_1$–$C_6$ groups, of which examples are methyl, ethyl, propyl, n-butyl, isobutyl, tert-butyl, n-pentyl, isopentyl, 1-methylbutyl, 1-ethylpropyl, neopentyl, tert-pentyl, n-hexyl and isohexyl. Among the preferred aryl groups are the $C_6$–$C_{18}$ aryl groups, examples of which are phenyl, nitrophenyl, chlorophenyl, methoxyphenyl, methylphenyl, dimethylphenyl, trimethylphenyl, naphthyl, naphthylphenyl and biphenyl. The preferred arylalkyl groups include $C_7$–$C_{20}$ arylalkyl groups such as benzyl and phenylethyl. The $R^1$ and $R^2$ substituents must be chosen so that they do not interfere in the oxidation reaction with molecular oxygen, and they should preferably contain no tertiary carbon atoms.

Secondary alcohols (reagent A) preferred as reactants for the first stage oxidation reaction producing hydrogen peroxide and ketones according to the invention are the aliphatic alcohols 2-propanol, 2-butanol, 2- and 3-pentanol, 2- and 3-hexanol, 2-, 3- and 4octanol, and 3,3'-dimethylbutan-2-ol and also the aromatic alcohols diphenylmethanol, 1-phenylethanol, 1-phenylpropanol, 1-phenylpropan-2-ol 1-phenylbutanol, 1-phenylbutan-2-ol, and 4-phenylbutan-2-ol.

In order to improve the first reaction's selectivity towards hydrogen peroxide, the oxidation of the secondary alcohol (reagent A) by molecular oxygen or air may be performed in the presence an additive: a primary alcohol and/or ether. Primary alcohol and/or ether 'additives' used in the first reaction are also referred to in this specification as 'reagent D'. Primary alcohols that may be used for this purpose are organic compounds which contain at least one carbon atom bonded to: two hydrogen atoms, a hydroxyl group and one organic radical; of the general formula:

$$R.CH_2OH$$

Examples of such primary alcohols are the $C_2$–$C_{16}$ primary aliphatic monoalcohols (e.g. ethanol, 1-propanol, 1-butanol, 1-pentanol, 1-hexanol, 1-octanol and 1-hexadecanol), the branched $C_4$–$C_{16}$ primary aliphatic monoalcohols (e.g. 2-methylpentanol, 2,2-dimethylpropanol, 3-methylbutanol, 2-ethylhexanol, and 2,2,4-trimethylpentanol), the aromatic alcohols (e.g. 2-phenylethanol, 2- and 3-phenylpropanol), and the diols and polyols (e.g. 1,4-butanodiol, 1,6-hexanodiol, and 1,1,1-tris[hydroxymethyl]propane).

The ethers which may be used as additives to improve the first reaction's selectivity towards hydrogen peroxide include organic compounds which contain at least one oxygen atom bonded to two organic radicals, of the general formula:

R.O.R

Examples of such ethers are the aliphatic ethers (e.g. diethyl ether, di-n-butyl ether), the ethyleneglycol ethers (e.g. ethyleneglycol dipropylether, ethyleneglycol dihexylether, ethyleneglycol diphenylether), the diethyleneglycol ethers (e.g. diethyleneglycol dimethylether, diethyleneglycol dibutylether), the triethyleneglycol ethers (e.g. triethyleneglycol dimethylether, triethyleneglycol dibutylether), the propyleneglycol ethers (e.g. propyleneglycol diphenylether), the dipropyleneglcol ethers (e.g. dipropyleneglcol diethylether), and the tripropyleneglycol ethers (e.g. tripropyleneglcol dimethylether). Further examples are the cyclic ethers such as tetrahydrofuran, dioxane, 1,3-dioxolane, the crown ethers, the aromatic ethers (e.g. dibenzyl ether), the polymeric ethers (e.g. poly[ethylene oxide], poly[propylene oxide], poly[ethylene oxide-co-propylene oxide]) and the alkyl and aryl derivatives of each of these types of ether. Yet further examples include ethers which contain other functional moieties and are stable under the reaction conditions of the secondary alcohol oxidation: this group of ethers includes ether molecules possessing a primary alcohol moiety (e.g. 2-oxyethanol, 2-[2-ethoxyethoxy]ethanol) and ether molecules that incorporate an ester moiety (e.g. diethyleneglycol diacetate, diethyleneglycol monoacetate, triethyleneglycol benzoate).

It is preferable that the primary alcohol and/or ether (reagent D) optionally present during the oxidation of the secondary alcohol (reagent A) contains no hydrogen atoms bonded to tertiary or benzyl carbon atoms. The weight ratio of secondary alcohol to additive (weight ratio of reagent A to reagent D) is not critical to obtain improved selectivity towards hydrogen peroxide in any particular oxidation reaction. The optimal ratio in an individual case will depend upon the nature of the selected alcohol and/or ether and upon the reaction conditions: those skilled in the art will be able to determine the optimal ratio for particular conditions by routine variation of the quantities of the selected additives. Generally the appropriate weight ratio of secondary alcohol (reagent A) to primary alcohol and/or ether (reagent D) will be between 90:10 and 10:90, and preferably being between 85:15 and 30:70.

Step II

The reaction mixture containing hydrogen peroxide from Step I is used as the oxidant for Step II, in which an unsaturated olefinic compound undergoes epoxidation by the hydrogen peroxide in the presence of a titanium catalyst supported on solid silica. The ability to use the reaction mixture from the first step directly as an ingredient of the second reaction, providing the peroxide for the epoxidation, permits great advantages in efficiency and cost-effectiveness, for no intermediate step is required in order to purify the peroxide.

The catalyst of titanium-impregnated, amorphous silica may be prepared by impregnation of silica having a specific surface area comprising between 50 and 900 $m^2/g$ with a solution of titanium alkoxide and/or titanocene in oxygenated organic solvent, followed by separation of excess solute and solvent from the solid phase residue. Optionally, the silica is additionally impregnated with a compound of an element such as germanium or vanadium. These elements may be incorporated onto the silica in a prior, separate step from the impregnation with titanium or the silica may be impregnated with all components together using a combined solution in the selected oxygenated organic solvent (reagent C), or subsequently in a separate step after the impregnation with titanium. his oxygenated organic solvent is also referred to in this specification as 'reagent C'.

The form of titanium supplied for the impregnation of the silica is preferably an alkoxide of titanium (with the alkoxide groups comprising between one and eight atoms of carbon) or a solution of a titanocene (with cyclopentadienyl or substituted cyclopentadienyl groups containing from five to ten carbon atoms) in an organic solvent (reagent C) at titanium concentrations of 0.05 to 2 moles/ litre. The titanium in solution should be adjusted in order to yield a final concentration of titanium in the catalyst of approximately 0.1 to 10% by weight. The impregnation may be performed in a single step or in multiple stages, according to known techniques of drying and calcining.

The impregnation medium for preparing the catalyst comprises, in addition to the titanium alkoxide and/or titanocene, the oxygenated organic solvent (reagent C). This oxygenated organic solvent (reagent C) contains an oxygen atom within the molecule: it is selected from the group of alcohols, ketones, glycols, ethers and esters. This solvent (reagent C) preferably remains liquid at normal temperatures and pressures: thus aliphatic and aromatic alcohols, ketones, glycols, ethers or esters containing up to eight carbon atoms are generally preferred, particularly alcohols such as methanol, ethanol, isopropanol, n-butanol, cyclohexanol, and the methylcyclohexanols and dirnethylcyclohexanols; the use of cyclohexanol is particularly recommended. Glycols (e.g. ethyleneglycol and propyleneglycol), ketones (e.g. dimethylketone and methylethylketone), ethers (e.g. diisopropyl ether, methyl-tert-butyl ether and tertahydrofuiran) and esters (e.g. methyl acetate and butyl acetate) may also be used as solvents for the impregnation step.

Salts of alkaline metals or of alkali-earth metals are capable of functioning as promoters of the desired catalytic action. Thus a salt of lithium, sodium, potassium, magnesium or calcium may also be included in the impregnation medium for generating the epoxidation catalyst. Such an epoxidation catalyst is obtainable by impregnation of the silica with a medium that additionally comprises the salt of the alkaline metal or of the alkali-earth metal at between approximately 0.01% and 0.1% by weight (weight of alkaline metal or alkaline earth metal per 100 g of silica). The promoter may be incorporated into the silica in a prior, separate step from the impregnation with titanium, or the silica may be impregnated with these components together, using a combined solution in the selected oxygenated organic solvent (reagent C). The promoter lowers the prevalence of oxirane ring-opening reactions during the epoxidation reaction by reducing the number of acidic centres on the surface of the catalyst, thereby altering the selectivity of the reaction towards the production of epoxide. The catalyst prepared according to the invention is particularly suitable for the epoxidation in liquid phase of the carbon-carbon double bonds of olefin compounds by organic solutions containing hydrogen peroxide.

The catalyst can be removed or replaced if the rate of reaction falls to a minimum acceptable level. Separation of the catalyst from the reaction mixture may be achieved by various methods known in the art, for example by filtration if the catalyst has been suspended in the reaction mixture. It may be desirable to replace and regenerate all or part of the catalyst present in the reactor on a periodic or continual basis, in order to maintain optimal values of activity and selectivity. The ease with which the titanium catalyst used in the process may be regenerated is an additional advantage of the invention. Appropriate techniques of regenerating such catalysts are known in the art and include calcination and treatment with solvents.

The carbon-carbon double bonds of olefin compounds that undergo epoxidation in the integrated process of the invention conform to the formula:

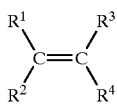

in which $R^1$, $R^2$, $R^3$ and $R^4$ may be hydrogen or halogen atoms, alkyl, aryl, cycloalkyl, arylalkyl radicals or carboxylate, ester, anhydro, sulphonate, nitryl or ether groups. The alkyl, aryl, cycloalkyl, arylalkyl radicals are also able to contain carboxylate groups, esters, sulphonic acids, nitryl, halogen hydroxyl groups or ketone moieties. The epoxidation reaction of the invention is generally capable of generating, using a solution of hydrogen peroxide, the epoxide of all olefin compounds that contain a non-aromatic carbon-carbon double bond.

A major group of olefin compounds that undergo epoxidation by hydrogen peroxide in the reactions coupled according to the invention are alkenes that contain between 2 and 18 atoms of carbon, such as ethylene, propylene, 1-butene, 2-bulene, isobutene, 1-hexene, 1-oxtene and 1-hexadecene. The process of the invention is particularly suitable for epoxidation of propylene and the $C_4$ olefins.

Cycloalkenes and substituted cycloalkenes constitute another class of olefin compounds that are able to undergo epoxidation according to the invention. Suitable cycloalkenes include cyclopentene, cyclohexene, cyclooctene and cyclododecene. Similarly, other cyclic olefin compounds possessing a carbon-carbon double bond are able to undergo epoxidation in the process of the invention (e.g. dicylopentadiene, cyclooctadiene and vinylcyclohexene), as are alkenes with aryl substitutions (e.g. styrene and divinylbenzene) and many of those olefin compounds that are unable to undergo epoxidation in reactions catalysed by microporous catalysts such as the zeolites because they are too voluminous to have access to the internal catalytic surfaces (e.g. norbornene).

The olefin compounds able of undergoing epoxidation according to the invention may also possess other functional groups adjacent to or remote from the carbon-carbon double bond, such as an alcohol moiety: for example, allyl alcohol and its esters, allyl chlorides and bromides, the acrylic acids, methylacrylic acids and their esters, fumaric acid, maleic acid or an ester or anhydride of these acids.

The epoxidation must be performed in the presence of a solvent with adequate capacity to dissolve or disperse the reactants and facilitate the control of the reaction temperature. This epoxidation solvent is also referred to in this specification as 'reagent B'. This solvent must be compatible with all the solvents and reagents from the first reaction at the concentrations in which they are added to the epoxidation mixture as part of the integrated process: note that each of the components of the first reaction will generally be of substantially greater polarity than either the olefin reagent or the epoxide product of the second, epoxidation reaction.

Preferred organic solvents for the epoxidation reaction (reagent B) are $C_6$ to $C_8$ aromatic alcohols (e.g. 1-phenylethanol and 2-phenylethanol) or $C_1$ to $C_8$ aliphatic alcohols (e.g. methanol, ethanol, n-butanol and hexanol), of which the most preferred is 2-methyl-2-propanol (tert-butanol).

The temperature of the epoxidation reaction is maintained between 30° C. and 140° C., and preferably between 60° C. and 100° C., which is adequate for selective conversion of the olefin to the epoxide in a short reaction time with minimal non-selective decomposition of hydrogen peroxide. Because of the high oxidising activity of hydrogen peroxide, precautions are necessary to avoid its participation in side-reactions with epoxidation products and solvents during the reaction and also during the enrichment and purification of the olefin epoxide. Consequently it is preferable to adjust the reaction conditions to obtain maximal conversion of the hydrogen peroxide present. The conversion rate should therefore be at least 90% and preferably at least 95%. The optimal temperature of the epoxidation reaction is determined by, among other factors, the concentration of catalyst, the reactivity of the olefin compound and its concentration, and by the type of solvent used. Generally residence times of between 10 and 300 minutes are adequate, being a function of the factors mentioned above. The reaction may be performed at atmospheric pressure, or at elevated pressure (typically between 0.1 MPa and 10 MPa) in order to maintain the components of the reaction mixture in liquid phase. Thus, when performing epoxidation of an olefin having a boiling point, at atmospheric pressure, less than the temperature of the epoxidation reaction, sufficient pressure must be applied to maintain the olefin in liquid phase: propylene is an example of such an olefin.

Working Examples

In order to illustrate the nature of the invention more fully, and the manner in which it is to be practised, the following examples are presented:

EXAMPLE 1

An oxidant solution was prepared by the oxidation of 1-phenylethanol (reagent A), in liquid phase at atmospheric pressure, and containing 2-methoxyethyl ether (reagent D) as disclosed in European Patent Application 0 839 760 A2. After reaction the solution contained approximately 4 wt % $H_2O_2$, with 80 % selectivity towards hydrogen peroxide.

EXAMPLE 2

An epoxidation catalyst was prepared by the following method. Tetraisopropyl orthotitanate (5.85 g) was added to 900 ml cyclohexanol (reagent C), with stirring, and the mixture heated to 150° C. To this solution was added powdered silica (30 g; Grace silica SP9-10214, having specific surface area of 301 $m^2/g$); the temperature and stirring were maintained for a further two hours. The suspension was then filtered, the solid residue washed with the 900 ml cyclohexanol and finally calcined under air at 500° C. for five hours. This preparation was used as the catalyst for the epoxidation of propylene as described immediately below.

A stirred, semi-continuous tank reactor was charged with the following: 12 g catalyst in pellet form diluted with glass pearls and placed within a porous basket, 192 g tert-butanol (reagent B) and 147 g propylene. The mixture was heated with stirring to 70° C. and then pressurised nitrogen gas was introduced to raise the reactor pressure to 36 bar. Oxidant solution (86 g; prepared as in Example 1, 3.2 wt % $H_2O_2$)

was then added to the stirred reaction mixture over a 30 minute period. Two hours after commencing the addition of oxidant solution 90 % of the hydrogen peroxide was converted, with the reaction demonstrating 90 % selectivity towards propylene oxide on the basis of hydrogen peroxide added.

EXAMPLE 3

An epoxidation catalyst was prepared by impregnating silica with a titanium compound as follows. Tetraisopropyl titanate (1.43 g) was mixed with 300 ml cyclohexanol (reagent C) while stirring and heating to 150° C. To this solution was added 9 g silica (Grace silica, specific surface area 300 m$^2$/g, pore volume 1.65 cm$^3$/g). The temperature and stirring were maintained for two hours. When the mixture subsequently cooled to ambient temperature the liquid was removed by filtration and the residue washed with cyclohexanol. The solid was calcined under air at 500° C. for five hours.

EXAMPLE 4

Oxidant solution (5.45 g; prepared as in Example 1, containing H$_2$O$_2$ at 4 wt %) was added dropwise to a stirred reactor containing titanium silica (1 g; prepared as in Example 3) and a mixture of 11 g tert-butanol (reagent B) and 0.2 mol norbornylene maintained at 70° C. Two hours after commencing the addition of oxidant solution 98 % of the hydrogen peroxide was converted, with the reaction demonstrating 83 % selectivity towards epoxide.

EXAMPLE 5

Oxidant solution (5.02 g; prepared as in Example 1, containing H$_2$O$_2$ at 4 wt %) was added dropwise to a stirred reactor containing titanium silicalite (1 g; prepared as in Example 3) and a mixture of 11 g tert-butanol (reagent B) and 0.2 mol cyclohexene maintained at 70° C. Two hours after commencing the addition of oxidant solution 98 % of the hydrogen peroxide was converted, with the reaction demonstrating 75 % selectivity towards epoxide.

EXAMPLE 6

Oxidant solution (6.06 g; prepared as in Example 1, containing H$_2$O$_2$ at 4 wt %) was added dropwise to a stirred reactor containing titanium silica (1 g; prepared as in Example 3) and a mixture of 11 g tert-butanol (reagent B) and 0.2 mol 1-octene maintained at 70° C. One hour after commencing the addition of oxidant solution 96 % of the hydrogen peroxide was converted, with the reaction demonstrating 85 % selectivity towards epoxide.

What is claimed is:

1. A continuous, integrated process for producing an organic epoxide comprising the following steps:
   (I) oxidation of a secondary alcohol (reagent A) by an oxidant selected from the group consisting of molecular oxygen and air;
   (ii) epoxidation of an olefin by admixing the reaction mixture of step (I) with a solution of the olefin in the presence of a catalyst at temperatures between 50° C. and 140° C.
   wherein
   the catalyst is an amorphous silica having a surface area between 50 m$^2$/g and 900 m$^2$/g impregnated with a solution selected from the group consisting of titanium alkoxide, titanocene and mixtures thereof in oxygenated organic solvent (reagent C).

2. The process according to claim 1 wherein the oxygenated organic solvent (reagent C) is selected from the group consisting of alcohols, ketones, glycols, ethers and esters that are liquid at normal ambient temperatures and pressure and that have fewer than nine carbon atoms.

3. The process according to claim 2 wherein the oxygenated organic solvent (reagent C) is selected from the group consisting of methanol, ethanol, isopropanol, n-butanol, tert-butanol, cyclohexanol, methylcyclohexanol and dimethylcyclohexanol.

4. The process according to claims 1, 2 or 3 wherein the epoxidation catalyst is obtainable by impregnation of the silica with a medium that comprises a salt selected from the group consisting of a salt of an alkaline metal and of an alkali-earth metal at between approximately 0.01% and 0.1% by weight (weight of alkaline metal or alkali-earth metal per 100 g of silica).

5. The process according to claim 4 wherein the oxidation of the secondary alcohol (reagent A) is performed entirely in liquid phase.

6. The process according to claim 1 wherein the oxidation of the secondary alcohol (reagent A) is performed in the presence of a compound selected from a group consisting of primary alcohols, ethers and mixtures thereof (reagent D).

7. The process according to claim 6 wherein, said compound (reagent D) that is present during the oxidation of the secondary alcohol (reagent A) contains neither hydrogen atoms bonded to tertiary nor benzyl carbon atoms.

8. The process according to claim 6 wherein the organic solution in which the secondary alcohol (reagent A) is oxidized comprises a weight ratio of secondary alcohol (reagent A) to said compound (reagent D) in the range between 90:10 and 10:90.

9. The process according to claim 1 wherein the oxidation of the secondary alcohol (reagent A) is performed:
   (I) at a temperature in the range between approximately 60° C. and 160° C.; and
   (ii) at overall pressures in the range between about 1 kg cm$^{-2}$ and 40 kg cm$^{-2}$.

10. The process according to claim 1 wherein a concentration of hydrogen peroxide in the range between 1% and 15% by weight is generated within the organic solution in which a secondary alcohol (reagent A) is oxidized.

11. The process according to claim 1 wherein the secondary alcohol (reagent A) is 1-phenylethanol.

12. The process according to claim 1 wherein the organic solvent in the epoxidation reaction (reagent B) is selected from a group consisting of methanol, ethanol, n-butanol, tert-butanol, hexanol, 1-phenylethanol and 2-phenylethanol.

13. The process according to claim 1 wherein the olefin is propylene.

14. The process according to claim 1 wherein:
   (I) said catalyst silica is further impregnated with a compound selected from a group consisting of germanium and vanadium.

15. The process according to claim 1 wherein the organic solvent is selected from a group consisting of:
   (ii) methanol, ethanol, 1-propanol, 1-butanol, 1-hexanol, 1-octanol and 1-hexadecanol, isopropanol, n-butanol, cyclohexane, cyclohexanol, methyl cyclohexanol, dimethylcyclohexanol, 2-methylpentanol, 2,2-dimethylpropanol, 3-methylbutanol, 2-ethylhexanol, 2,2,4-trimethylpentanol, 2-phenylethanol, 2- phenyl propanol, 3-phenylpropanol, 1,4-butanodiol, 1,6-hexanodiol, and 1,1,1-tris(hydroxymethyl)propane.

16. The process according to claim 1 wherein the organic solvent is selected from a group consisting of:

(I) dimethylketone and methylethylketone.

17. The process according to claim 1 wherein the organic solvent is selected from a group consisting of:
(i) ethyleneglycol and propyleneglycol.

18. The process according to claim 1 wherein the organic solvent is selected from a group consisting of:
(i) ethyleneglycol dipropylether, ethyleneglycol dihexylether, ethyleneglycol diphenylether, diethyleneglycol dimethylether, diethyleneglycol dibutylether, triethyleneglycol dimethylether, triethyleneglycol dibutylether, propyleneglycol diphenylether, dipropyleneglcol diethylether, tripropyleneglcol dimethylether, tetrahydrofuran, dioxane, 1,3-dioxolane, di-n-butyl ether, dibenzyl ether, poly (ethylene oxide), poly (propylene oxide), poly (ethylene oxide-co-propylene oxide), 2-oxyethanol, 2-(2-ethoxyethoxy) ethanol, diethyleneglycol diacetate, diethyleneglycol monoacetate, triethyleneglycol benzoate, diisopropyl ether, methyl-tert-butyl ether and tertahydrofuran.

19. The process according to claim 1 wherein the organic solvent is selected from a group consisting of:
(I) methyl acetate and butyl acetate.

20. The process according to claim 1 wherein said secondary alcohol is selected from a group consisting of:
(i) 2-propanol, 2-butanol, 2-pentanol, 3-pentanol, 2-hexanol, 3-hexanol, 2-octanol, 3-octanol, 4-octanol, 3,3'-dimethylbutan-2-ol, diphenylmethanol, 1-phenylethanol, 1-phenylpropanol, 1-phenylpropan-2-ol, 1-phenylbutanol, 1-phenylbutan-2-ol and 4-phenylbutan-2-ol.

21. The process according to claim 1 wherein the olefin is selected from a group consisting of:
(i) ethylene, propylene, 1-butene,2-bulene, isobutene, 1-hexene, 1-oxtene, 1-hexadecene, propylene, cyclopentene, cyclohexene, cyclooctene, cyclododecene, dicylopentadiene, cyclooctadiene, vinylcyclohexene, styrene, divinylbenzene, norbornene, allyl alcohol, allyl chlorides, allyl bromides, acrylic acid, methylacrylic acid, fumaric acid and maleic acid.

22. In a process for producing an epoxide from a secondary alcohol and an olefin utilizing a catalyst; the improvement comprising:
(i) said catalyst being an amorphous silica impregnated with a titanium compound.

23. A continuous, integrated process for producing an organic epoxide comprising the steps of:
(i) contacting a secondary alcohol (reagent A) with molecular oxygen or air to form an oxidant mixture comprising the secondary alcohol and hydrogen peroxide; and
(ii) contacting the oxidant mixture of step (i) with an olefin and a catalytically effective amount of a titanium catalyst supported on amorphous silica, at a temperature between 50° C. and 140° C., to convert the olefin to the epoxide, characterized in that said titanium catalyst is obtained by impregnating a silica having a surface area between 50 $m^2/g$ and 900$m^2/g$ with a solution of titanium alkoxide and/or titanocene in an oxygenated organic solvent (reagent C), said titanium catalyst supported on amorphous silica.

* * * * *